US006238357B1

(12) United States Patent
Kawaguchi et al.

(10) Patent No.: US 6,238,357 B1
(45) Date of Patent: May 29, 2001

(54) HEALTH APPLIANCE INCLUDING AN EXPANDABLE CHAMBER FOR STRETCHING THE TOES

(75) Inventors: Hirozumi Kawaguchi; Takehiko Satsu, both of Arita (JP)

(73) Assignee: Kawaei Co., Ltd., Wakayama (JP)

( * ) Notice: Subject to any disclaimer, the term of this patent is extended or adjusted under 35 U.S.C. 154(b) by 0 days.

(21) Appl. No.: 09/268,697

(22) Filed: Mar. 16, 1999

(30) Foreign Application Priority Data

Mar. 17, 1998 (JP) ........................................ 10-067266
Feb. 18, 1999 (JP) ........................................ 11-039632

(51) Int. Cl.7 ........................ A61H 9/00; A61F 5/042

(52) U.S. Cl. ........................ 601/27; 601/40; 601/148; 602/13; 602/30; 128/DIG. 20

(58) Field of Search .................. 601/27, 40, 148–152; 602/30, 13, 22; 132/73, 285; D28/61, 56, 57; D21/440; 446/221; 128/DIG. 20, 893

(56) References Cited

U.S. PATENT DOCUMENTS 2,095,664 * 10/1937 Grenfell .
2,249,298 * 7/1941 Ratti .
3,429,309 * 2/1969 Kurth et al. .
4,182,320 * 1/1980 Sweeney .
4,207,880 * 6/1980 Zinkovich .
4,522,197 6/1985 Hasegawa .
4,706,658 * 11/1987 Cronin .
4,941,458 7/1990 Taheri .
5,076,263 12/1991 Funatogawa .
5,607,749 * 3/1997 Strumor .

FOREIGN PATENT DOCUMENTS 0 261 481 3/1988 (EP) .
2 531 630 2/1984 (FR) .
2 147 812 5/1985 (GB) .
2 266 843 11/1993 (GB) .

* cited by examiner

*Primary Examiner*—Danton D. DeMille
(74) *Attorney, Agent, or Firm*—Wenderoth, Lind & Ponack, L.L.P.

(57) ABSTRACT

A health appliance comprises a fitting member fittable in between toes or fingers and having in an interior thereof a pressurized medium charging portion. This portion is expanded in a direction so as to widen a space between the toes or fingers when the pressurized medium is charged therein. A pressurized medium charging port is provided at a location of the health appliance so as to communicate with the fitting member, for charging the pressurized medium into the pressurized medium charging portion.

10 Claims, 8 Drawing Sheets

HEALTH APPLIANCE INCLUDING AN EXPANDABLE CHAMBER FOR STRETCHING THE TOES

BACKGROUND OF THE INVENTION

1. Field of the Invention

The present invention relates to a health appliance for use in stretching fingers or toes so as to stretch their muscles at the webs. This stretching improves circulation of the blood, so as to increase one's health.

2. Description of the Prior Art

One's toes are kept in a fixed state in a shoe used as a footwear. Therefore, the muscles of the toes at the webs are constricted so as to cause hindrance of the circulation of the blood at the tip of one's foot. Wearing shoes for a long time worsens the circulation of the blood, so that one's leg swells or feels heavy, leading to fatigue.

It is generally known that a stretch of the toes improves the circulation of the blood at the webs and is effective for recovery from fatigue and for promotion of health. When one's leg feels heavy, for example, he usually massages his toes by rubbing, kneading or stretching the toes with his hands, to improve the circulation of the blood at the webs. However, massaging one's toes with his own hands to improve the circulation of the blood at the webs requires a tiresome labor and makes his hands dull.

For improving the circulation of the blood at the webs without tiresome labor, health appliances for use in stretching toes are proposed. A typical type of health appliance has cylindrical spongy members to be fitted in between toes to stretch them and keep them in the stretched state.

However, this type of health appliance has the disadvantage that since the cylindrical members are required to have a thickness large enough to let the toes stretch widely, they are hard to be fitted into limited spaces to expand, such as spaces between the toes.

It also has the disadvantage that the spaces between the toes stretched by use of this type of health appliance are limited by the thickness of the cylindrical members of the health appliance, so that the spaces cannot be varied or adjusted arbitrarily. In addition, it is desired that not only a space(s) between the toes but also a space(s) between fingers can be widened to any desired amount to stretch the muscles of the fingers at the webs, so as to improve the circulation of blood.

SUMMARY OF THE INVENTION

In the light of the disadvantages involved in the prior art mentioned above, the present invention has been made, with the aim of providing a health appliance which enables the muscles of the toes or fingers at the webs to be reliably stretched to improve the circulation of the blood without doing any tiresome labor; enables a fitting member(s) of the health appliance to be easily held in a sandwich relation between the toes or fingers; and, further, enables the space(s) between the toes or fingers to be increased or decreased arbitrarily.

To accomplish the object above, the present invention provides a novel health appliance comprising a fitting member fittable between toes or fingers. The fitting member has in an interior thereof a pressurized medium charging portion (charging chamber) which is expanded in a direction for a space between the toes or fingers to be widened when the pressurized medium is charged therein. The appliance also comprises a pressurized medium charging port, provided at a location of the health appliance communicating with the fitting member, for charging the pressurized medium into the pressurized medium charging portion.

In this arrangement, there may be provided only one or two or more fitting members to be fitted in between any two neighboring toes or fingers, and no particular limitation is imposed on the number of fitting members.

The provision of a single fitting member provides the advantages that the health appliance can be made compact and also the fitting member can be selectively fitted in between only the toes or fingers at the web at which the circulation of the blood is desired to be improved.

The provision of two or more fitting members provides the advantage that three or more toes or fingers at the webs can be stretched at one stroke with efficiency, and the circulation of the blood can be improved by the synergistic effect.

The fitting members provided may include any number of fitting members. For example, four fitting members for all five toes or fingers of one foot or hand; five or more fitting members for toes or fingers of both feet or hands; and two or three fitting members for toes and fingers at any selected location of one foot or hand.

Also, the health appliance may be in the form of the fitting member only (i.e., the fitting member having the pressurized medium charging port only), or the fitting member(s) combined with other member(s). In fact, no particular limitation is imposed on the form of the health appliance.

In addition, the fitting member may take any configuration including a cylinder, a sphere, or a polygonal prism into which the fitting member will be shaped when expanded, or a configuration formed by lamination of a thin film and a thin plate or the like. No particular limitation is imposed on the configuration of the fitting member.

Further, no particular limitation is imposed on the materials of the pressurized medium charging portion, as long as the materials have hermeticity or airtightness and flexibility. The materials which may be used for forming a hollow case-like member include hermetic non-woven fabrics made of plastics, such as polyester, nylon, and polyurethane, hermetic textiles formed of synthetic resins, or sheet-like materials made of rubbers or plastics.

It is to be noted here that the fitting member may be formed by a combination of two or more different materials, as in the form in which the pressurized medium charging portion is formed around a rigid core or the form in which a protecting cover is formed around the pressurized medium charging portion. The fitting member may also be formed by only one type of material, as in the form in which the pressurized medium charging portion is formed by the interior of the case formed of only a hermetic non-woven fabric of polyurethane, for example, so that the case itself can be formed as the fitting member.

Further, the pressurized mediums which may be used include a gas such as air, a liquid such as water or oil, or a semi-solid having flowability like sol. As long as the pressurized medium has such a kinetic property as to be freely fed into the pressurized medium charging portion in the fitting member, no particular limitation is imposed on the pressurized mediums.

The pressurized medium charging port may be located directly in the fitting member or in another portion of the health appliance, and no particular limitation is imposed on the location of the pressurized medium charging port. Additionally, there may be provided a valve, such as a safety valve or a relief valve, for regulating the pressure of the pressurized medium to a predetermined value.

The health appliance may include a base member. The base member comprises a back contacting member which is arranged to contact a sole of a foot or a palm of a hand and/or a front contacting member which is arranged to contact an instep of the foot or a back of the hand. The fitting member is fixed to the back contacting member and/or the front contacting member.

In this arrangement, no particular limitation is imposed on the configuration of the back contacting member or the front contacting member, as long as it has such configuration as to be contactable with the sole of the foot or the palm of the hand or the instep of the foot or the back of the hand.

The materials which may be used for forming the back contacting member or the front contacting member include a plate-like member formed of wood, metal or synthetic resin, and a mat or a case formed of natural fiber or synthetic fiber. The plate-like member is preferably made to have elasticity, like a rubber plate. Further, the back contact member contactable with the sole of the foot may be provided with undulation which is matched with the shape of the sole of the foot, or may be provided with projections which can arouse massaging points in the sole of the foot.

The front contacting member and/or the back contacting member have in an interior thereof a pressurized medium charging portion which is expanded when the pressurized medium is charged therein. This expansion presses a tip portion of the foot and/or a tip portion of the hand contacting the front contacting member and/or the back contacting member. A pressurized medium charging port for charging the pressurized medium into the pressurized medium charging portion is provided at a location of the health appliance communicating with the front contacting member and/or the back contacting member.

The pressurized medium charging portion of the front contacting member, the pressurized medium charging portion of the back contacting member, and the pressurized medium charging portion in the fitting member may be integrally formed. Therefore, when the pressurized medium is charged into the pressurized medium charging portions and the fitting member is fitted in between the toes and/or fingers, the fitting member is expanded in a direction so as to increase a space between the toes or fingers. In addition, the front contacting member and the back contacting member are expanded to press the tip portion of the foot and/or the tip portion of the hand from both sides of the instep of the foot and/or the back of the hand and the sole of the foot and/or the palm of the hand.

Also, the present invention provides a health appliance comprising a fitting member fittable in between toes or fingers. In an interior of the appliance is a first pressurized medium charging portion; a back contacting member which has a second pressurized medium charging portion communicating with the first pressurized medium charging portion, and which is contactable with a sole of a foot or a palm of a hand; and/or a front contacting member which has a third pressurized medium charging portion communicating with the first pressurized medium charging portion and is contactable with an instep of the foot or a back of the hand. Therefore the pressurized medium charged in the second pressurized medium charging portion and/or the pressurized medium charged in the third pressurized medium charging portion is allowed to move to the first pressurized medium charging portion by pressing the back contacting member and/or the front contacting member from outside. This expands the fitting member in a direction so as to widen the space between the toes or fingers.

DETAILED DESCRIPTION OF THE EMBODIMENT

Referring now to the accompanying drawings, examples of the preferred embodiments of the present invention directed to a health appliance will be described below. It is to be understood, however, that the scope of the invention is by no means limited to the illustrated embodiments.

Figure 1:
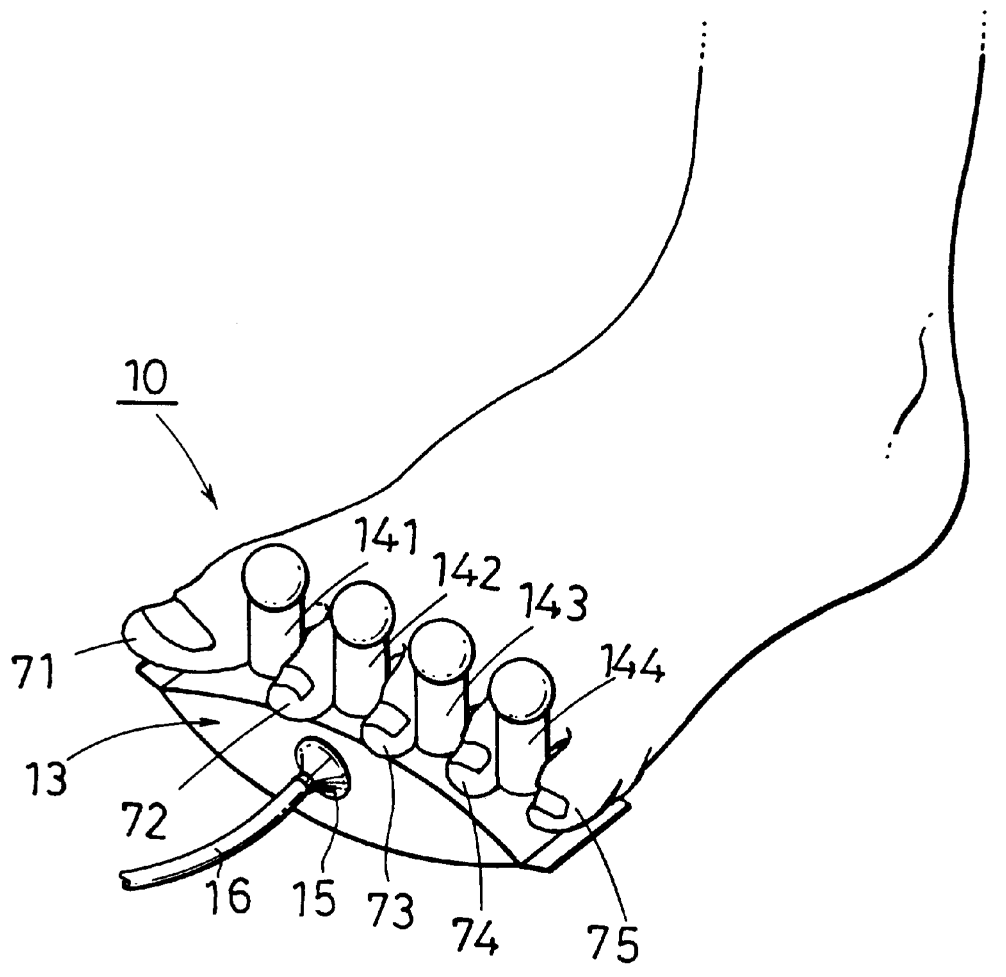
FIG. 1 is a perspective view of one embodied form of the health appliance according to the invention as is fitted to the toes and charged with a pressurized medium.

As shown in FIG. 1, a health appliance 10 comprises aback contacting member 13 which can contact the sole of the foot, fitting members fittable in between the toes (hereinafter they are simply referred to as "fitting members") 141, 142, 143 and 144, and a pressurized medium charging port 15 (hereinafter it is simply referred to as "charging port").

The overall health appliance 10 including the back contacting member 13 and the fitting members 141, 142, 143 and 144 is formed of a hermetic non-woven fabric made of urethane and has in an interior thereof a pressurized medium charging portion (charging chamber), not shown.

The back contacting member 13 has a configuration like a horizontally elongated bag or case, and the pressurized medium charging port 15 provided at the back contacting member 13 is adapted to be capable of connecting with an air supply hose 16 for supplying the air of the pressurized medium to the back contacting member.

The fitting members 141, 142, 143 and 144 are held by the back contacting member 13, and are spaced in series at intervals generally equal to the thickness of the toes 72, 73, and 74. Therefore, they can be fitted in the spaces between the toes 71, 72, 73, 74 and 75.

Also, the fitting members 141, 142, 143 and 144 are adapted to expand to a larger extent at their upper portions extending beyond the toes than at their portions existing in between the toes 71–75, when expanded.

The fitting member 141 to be fitted in between the toe 71 (first toe) and the toe 72 (second toe) is made larger in diameter than the remaining fitting members 142–144 to be fitted in between the remaining toes, for a further stretch of the toes 71, 72.

Now, the use and operation of the health appliance 10 will be described below. First, the health appliance is attached to the tip portion of the foot by fitting the fitting members 141–144 in between the toes 71–75 before the air of the pressurized medium is charged into the fitting members, though not shown. After the air supply hose 16 is connected to the charging port 15, the air is charged from the charging port 15. Then, the back contacting member 13 and the fitting members 141–144 are expanded, as shown in FIG. 1, so that the spaces between the toes 71, 72, 73, 74 and 75 or their web portions are spread or stretched out. After the toes 71–75 are stretched out at the webs to a given extent, the stretched state of the toes 71–75 at the webs is maintained for a certain time by regulating the amount of air supplied through the air supply hose in such a manner that the air charged from the charging port 15 can be made equal in pressure to the air discharged therefrom. After the stretched state is maintained for a certain time, the air supply given through the air supply hose is stopped. An air discharging passage for allowing the air to be discharged from the charging port 15 is secured so as to discharge the air from the charging port 15. The steps above are repeated for a desired number of times.

According to the health appliance 10 thus constructed, since the fitting members 141–144 remain in reduced diameters before they are charged with the air, the fitting members 141–144 can be easily fitted in between the toes 71–75 with so as to be held in sandwich relation therebetween.

Also, according to the health appliance 10, a simple operation of charging the air from the charging port 15 can allow the toes to be stretched out with ease, so as to improve the circulation of the blood in the webs.

Further, according to the health appliance 10, the spaces (widths) between the toes 71–75 can be varied arbitrarily by varying the degree of expansion of the fitting members 141–144, so that the muscles of the toes at the webs can be stretched comfortably. Since the fitting members 141–144, when fitted in between the toes 71–75, are expanded more at the upper portions extending beyond the toes, the fitting members can be prevented from being slipped out of the corresponding spaces of the toes 71–75 in the process of the expansion.

Next, another embodiment of the health appliance 1 will be described below.

Figure 2:
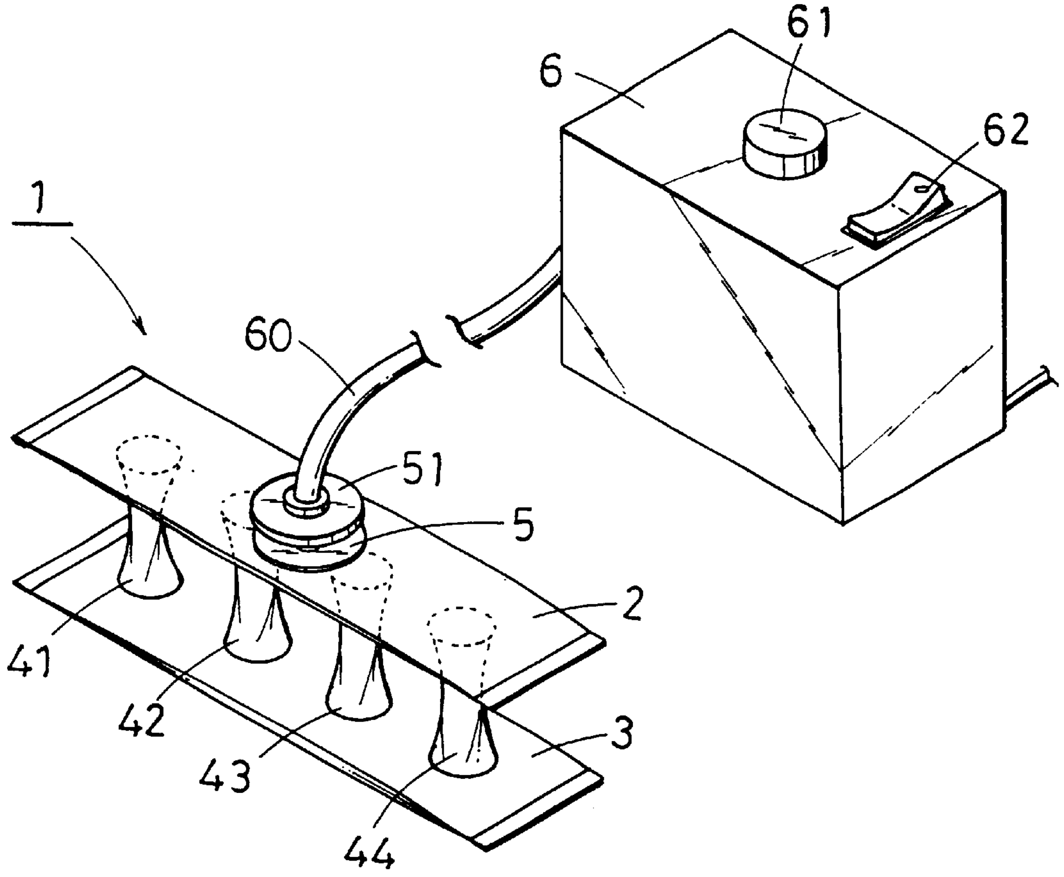
FIG. 2 is a perspective view of another embodied form of the health appliance according to the invention.
Figure 3:
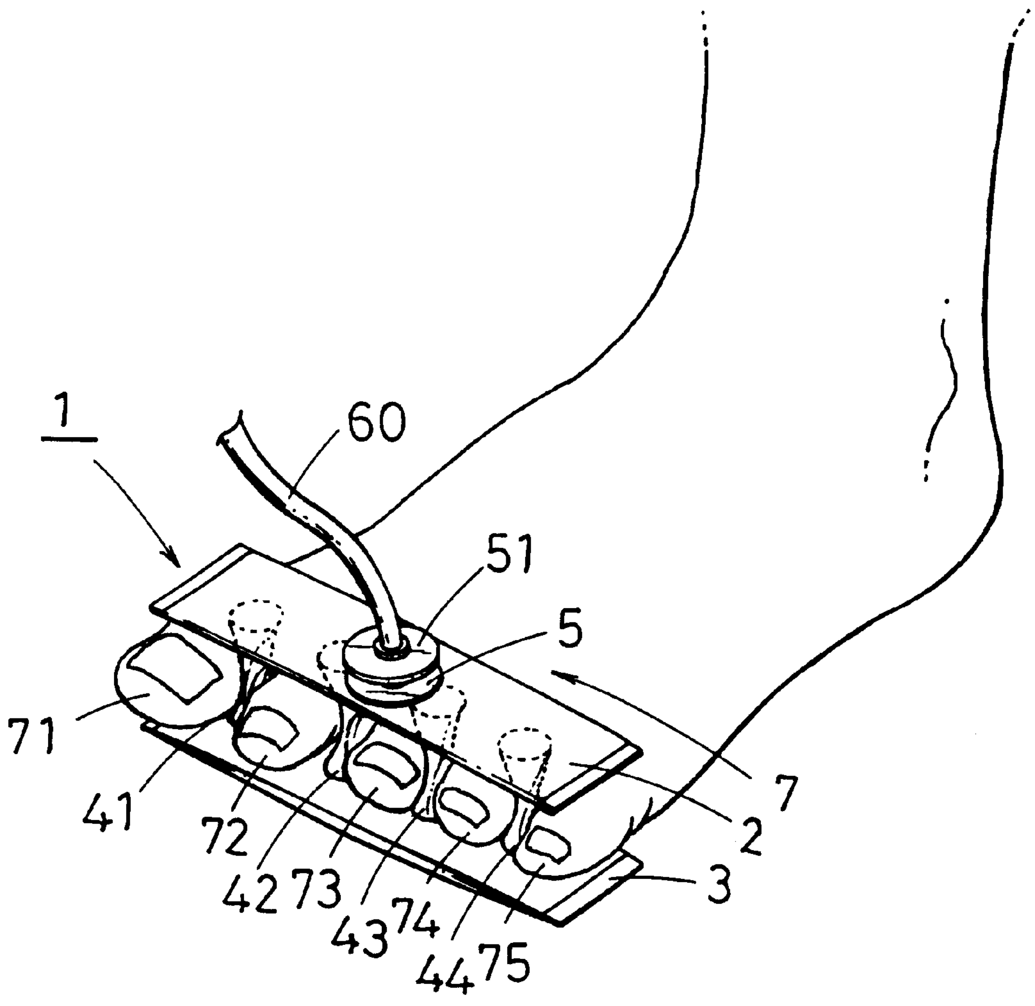
FIG. 3 is a perspective view of the health appliance of FIG. 2 as is fitted to the toes but not charged with the pressurized medium.
Figure 4:
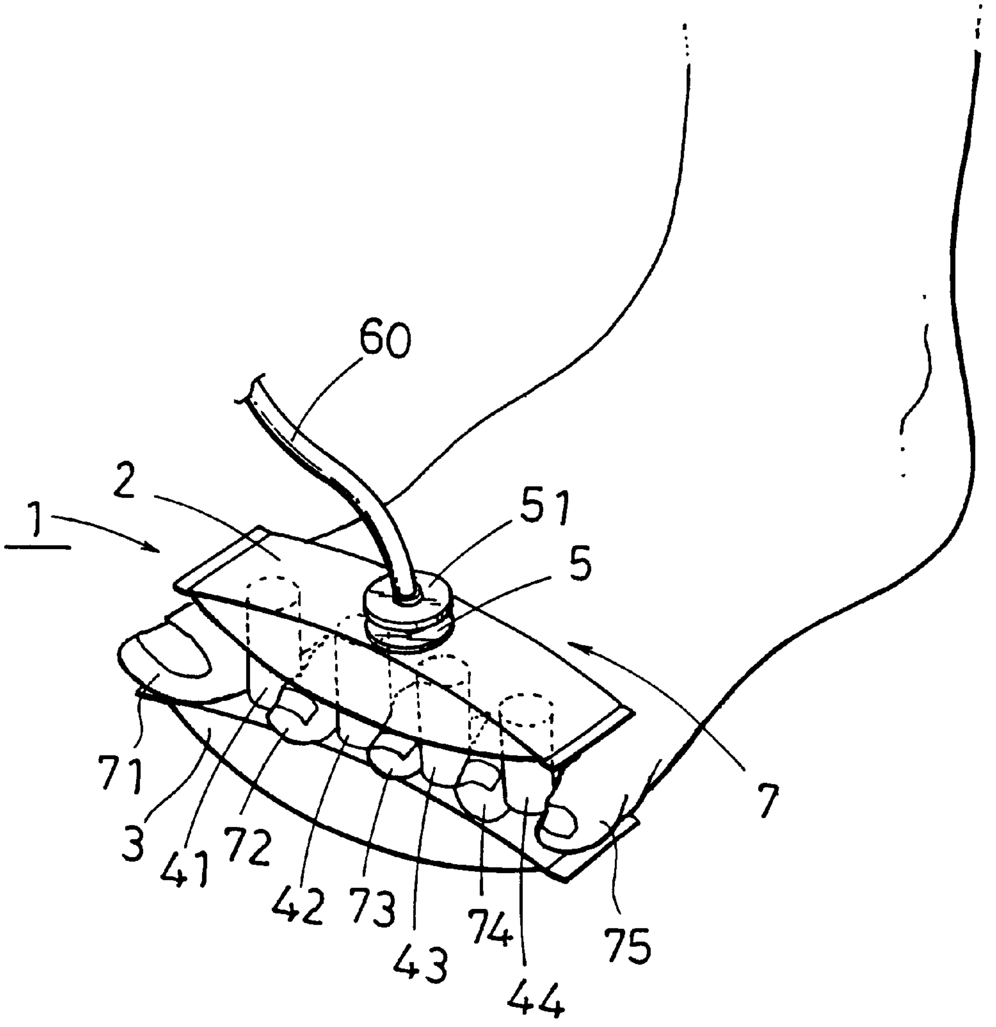
FIG. 4 is a perspective view of the health appliance of FIG. 2 as is fitted to the toes and charged with the pressurized medium.

As shown in FIGS. 2, 3 and 4, the health appliance 1 comprises a front contacting member 2 which can contact the instep, a back contacting member 3 which can contact the sole of the foot, fitting members insertable in between the toes (hereinafter they are simply referred to as "fitting members") 41, 42, 43 and 44, and a pressurized medium charging port 5 (hereinafter it is simply referred to as "charging port").

The overall health appliance 1 including the front contacting member 2, the back contacting member 3, and the fitting members 41, 42, 43 and 44 is formed of a hermetic non-woven fabric made of polyester, nylon or other synthetic resin, a synthetic rubber sheet, or a hermetic textile formed of synthetic resin fibers. The appliance has in an interior thereof a pressurized medium charging portion, not shown.

The front contacting member 2 has a configuration like a horizontally elongated bag, and is provided with the charging port 5. The air from the charging port 5 as the pressurized medium is charged into the pressurized medium charging portion in the interior of the health appliance 1. The charging port 5 is provided with an instantaneous exhaust valve 51.

The charging port 5 is adapted to be capable of being connected to an air supply hose 60 for supplying therethrough the air (the pressurized medium) fed from an air compressor 6 which is an air supply means.

The fitting members 41, 42, 43 and 44 are cylindrical in shape. The fitting members are each fixed to the front contacting member 2 at one end thereof and to the back contacting member 3 at the other end thereof. The fitting members are held between the front and back contacting members, and are spaced in series at such intervals so as to be easily fitted in between the toes.

The back contacting member 3 has a configuration like a horizontally elongated bag, and so does the front contacting member 2.

Thus, the health appliance 1 is so designed that the front and back contacting members 2, 3 can hold the tip end portion of the foot 7 in sandwich relation from both vertical sides thereof, with the fitting members 41, 42, 43 and 44 fitted in between the toes 71, 72, 73, 74 and 75 at their webs, respectively, as shown in FIGS. 3 and 4.

When the health appliance 1 is charged with the air fed from the charging port 5, the fitting members 41, 42, 43 and 44 are expanded in the direction so that the toes 71, 72, 73, 74 and 75 are stretched at their webs. In addition, the front contacting member 2 and the back contacting member 3 are expanded in the direction for the instep and the sole of the foot at the tip end portion 7 to be pressed, as shown in FIG. 4. The instantaneous exhaust valve 51 is designed so that when the pressure of the air charged in the pressurized medium charging portion of the health appliance 1 reaches a preset pressure, the air filled in the pressurized medium charging portion can be exhausted instantaneously through it.

The air compressor 6 is operated by an electric motor and has a compressed air exhausting portion, not shown, which can be connected with the air supply hose 60 so that the compressed air can be charged through the air supply hose 60 into the pressurized medium charging portion in the health appliance 1. The air compressor 6 is structured so that the pressure of the compressed air to be fed can be adjusted and an air supply mode and an air supply stop mode can be alternated at any selected intervals.

Now, the use and operation of the health appliance 1 will be described below. First, the air supply hose 60 is connected with the compressed air exhausting portion of the air compressor 6 at one end and is connected with the charging port 5 of the health appliance 1 at the other end, as shown in FIG. 2. Then, the health appliance 1 is attached to the tip portion of the foot so that the fitting members 41, 42, 43 and 44 can be fitted in the spaces between the toes, respectively, as shown in FIG. 3. Thereafter, the pressure of the compressed air to be fed from the air compressor 6 and the time intervals at which the air supply mode and the air supply stop mode are alternated are preset on a voluntary basis and then the air compressor 6 is powered.

The health appliance 1 is put into the expanded state, as shown in FIG. 4, by the compressed air fed from the air compressor 6 being charged from the charging port 5 into the pressurized medium charging portion. The appliance 1 is put into the contracted state, as shown in FIG. 3, by the air charged in the pressurized medium charging portion being exhausted from the instantaneous exhaust valve 51. The expansion and the contraction of the health appliance is repeated.

When the health appliance is put into the expanded state, as shown in FIG. 4, the toes 71, 72, 73, 74 and 75 are stretched at their webs, and the tip portion of the foot 7 is simultaneously pressed by the expanded front contacting member 2 and the expanded back contacting member 3.

On the other hand, when the health appliance is put into the contracted state, as shown in FIG. 3, the toes 71, 72, 73, 74 and 75 stretched at their webs are restored to the original state of being neither stretched nor pressed.

Thus, the health appliance 1 is expanded and contracted by charging and discharging the compressed air. Thereby, the stretched/pressed state of the toes 71, 72, 73, 74 and 75 and the tip portion 7 of the foot and the release from the stretched/pressed state are alternated at selected time intervals. This can produce a sort of finger-pressure massage of the tip portion of the foot, in addition to the effect of stretching the muscles of the toes at the webs, thus producing a further improved circulation of blood to relax the fatigue of one's foot.

The fitting members 41, 42, 43 and 44 are spaced in series at intervals corresponding to the intervals of the toes (i.e., the space between the toes) and are held by the front contacting member 2 and the back contacting member 3. This arrangement can provide the effects of enabling the fitting members 41, 42, 43 and 44 to be fitted in between the toes at their webs with facility and enabling the fitting members 41, 42, 43 and 44 to be prevented from being out of position with stability.

It should be noted that the time interval during which the health appliance 1 is kept in its expanded state may be determined on a voluntary basis to suit the user's liking, and the pressure at which the compressed air is charged to expand the health appliance 1 may also be adjusted on a voluntary basis.

In the embodied forms illustrated above, the fitting members are fixed to either the front contacting member 2 or the back contacting member 3 or both of them. However, as long as there is provided at least one fitting member which is fittable in between the toes and is expandable in the direction of the toes being stretched, the object of the invention can be accomplished.

A hand-operated air pump may, of course, be used as a substitute for the air compressor 6 so as to expand the health appliance 1, 10. This enables a more delicate regulation of the expanding pressure for the health appliance.

Also, instead of the instantaneous exhaust valve 51 provided at the charging port, an exhausting means may be provided at the air compressor 6 or at the hand-operated air pump so that the air charged in the pressurized medium charging portion can be exhausted by the exhausting means.

Advantageously, the health appliance should be adapted to be useable under the condition that the pressurized medium charging portion is filled with a heated pressurized medium, or under the condition that the foot is dipped in a warm bath. Therefore, a further improved circulation of the blood by the thermal effect can be added to make a better recovery from the fatigue of the foot.

Figure 9:
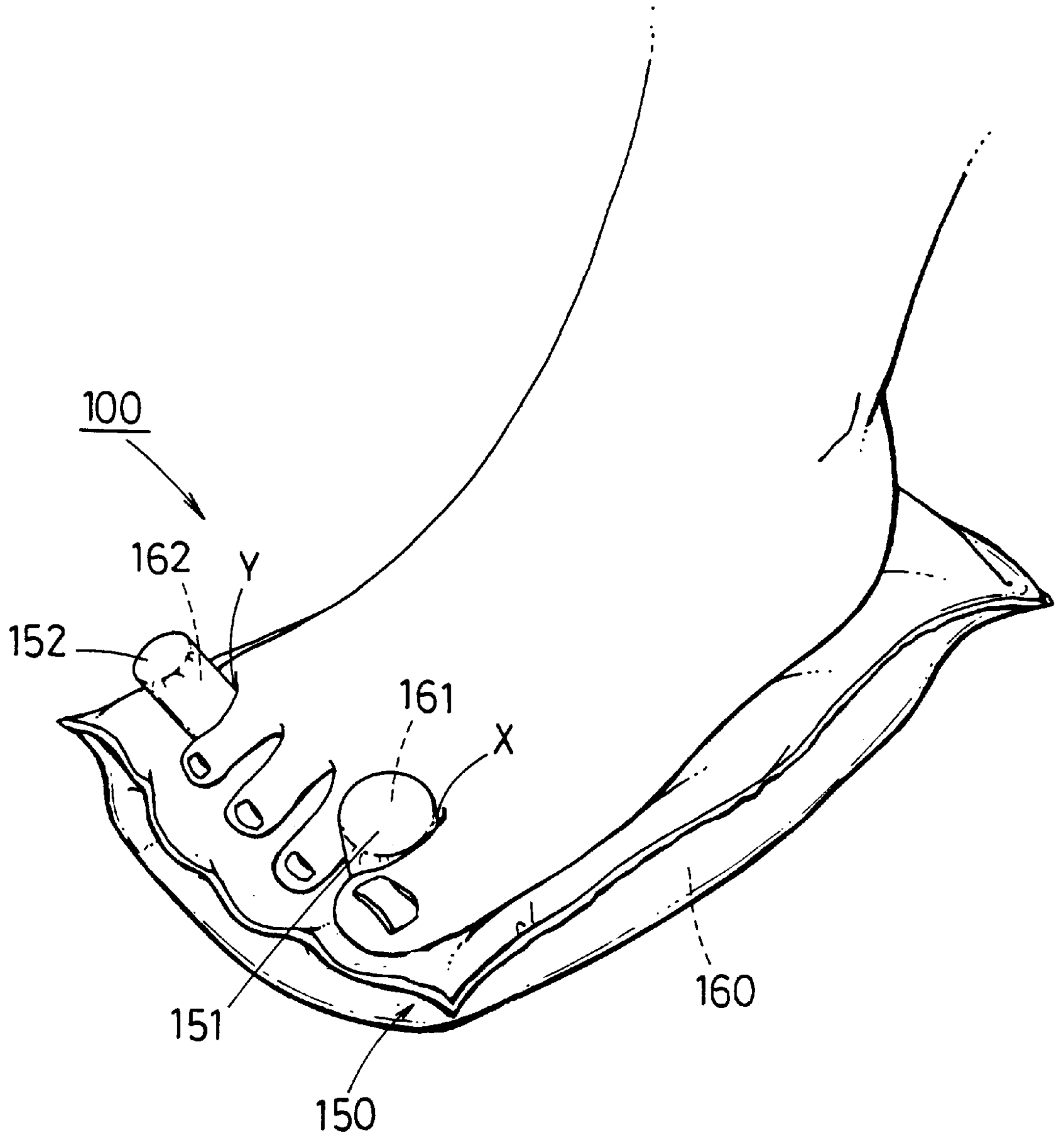
FIG. 9 is a perspective view showing a modified embodiment of the health appliance according to the invention.

Further, the health appliance according to the present invention is not limited to the embodied forms illustrated above. For example, the present invention may take the embodied form of the health appliance 100 as shown in FIG. 9, as a substitute for the illustrated health appliance 1, 10.

The health appliance 100 comprises a first fitting member 151, a second fitting member 152 and a back contacting member 150 which are formed in one piece. Of course, the first fitting member 151, the second fitting member 152 and the back contacting member 150 may be formed separately from each other so that the first and second fitting members 151, 152 can be fixed to the back contacting member 150 in such a manner as to communicate with the back contacting member 150.

The first fitting member 151 is formed of resin having hermeticity and is provided in an interior thereof with a first pressurized medium charging portion 161. Also, the first fitting member is disposed at a position at which the web X between the first toe and the second toe will correspond when the sole of the foot is placed on the back contacting member 150.

The second fitting member 152 is formed of resin having hermeticity and is provided in an interior thereof with a first pressurized medium charging portion 162. Also, the second fitting member is disposed at a position at which the web Y between the forth toe and the little toe will correspond when the sole of the foot is placed on the back contacting member 150.

The back contacting member 150 is formed of resin having hermeticity and formed into a hollow mat having a size generally corresponding to the sole of the foot. The back contacting member 150 is provided in an interior thereof with a second pressurized medium charging portion 160 in which a gel form matter is charged as the pressurized medium.

The second pressurized medium charging portion 160 communicates with the first pressurized medium charging portions 161, 162 so that the gel form matter charged in the second pressurized medium charging portion 160 can freely move to the first pressurized medium charging portions 161, 162.

In using the health appliance 100 thus constructed, the first fitting member 151 is fitted at the web X, and the second fitting member 152 is fitted at the web Y. Then the back contacting member 150 is pressed or eased up with the sole of the foot, to apply pressure thereon or release the pressure therefrom.

Specifically, when the back contacting member 150 is pressed with the sole of the foot to apply pressure thereon, the gel form matter charged in the second pressurized medium charging portion 160 moves to the first pressurized medium charging portions 161, 162 to expand the first fitting member 151 and the second fitting member 152. The webs X and Y are stretched out by the expansion of the first and second fitting members 151, 152.

When the expansion caused by the gel form matter in the first and second fitting member 151, 152 is reduced by reducing the pressure applied on the back contacting member 150, the stretched webs X and Y are restored to their original state.

When the back contacting member 150 is pressed again with the sole of the foot, the gel form matter charged in the second pressurized medium charging portion 160 is fed to the first pressurized medium charging portions 161, 162. As a result, the first fitting member 151 and the second fitting member 152 are expanded again to stretch the webs X and Y.

With this health appliance 100, the operations above are repeated. Thereby the toes can be stretched or restored to the initial state at a simple 17 pumping operation to improve the circulation of the blood in the webs X, Y.

In addition, this specific configuration can advantageously allow the health appliance 100 to be used as a pad or equivalent to be laid on an insole of a shoe or a slipper. The health appliance 100 may also be modified so as to have only one fitting member or three or more fitting members as a substitute for the two fitting members of the first and second fitting members 151, 152.

Further, in the health appliance 100, the back contacting member 150 may be provided in an interior thereof with a biasing means for biasing the back contacting member 150 in an expanding direction thereof. The biasing means which may be used include a coil spring, a blade spring or a sponge having high resiliency. With this modification in which the back contacting member 150 is provided in the interior thereof with the biasing means, the pressurized medium can be forcibly restored from the first pressurized medium charging portion to the second pressurized medium charging portion by weakening the pressure applied from the outside of the back contacting member.

Additionally, in the structure of the health appliance 100, a check valve may be assembled in the back contacting member 150 for allowing the pressurized medium to move to the fitting members to expand them.

Figure 10:
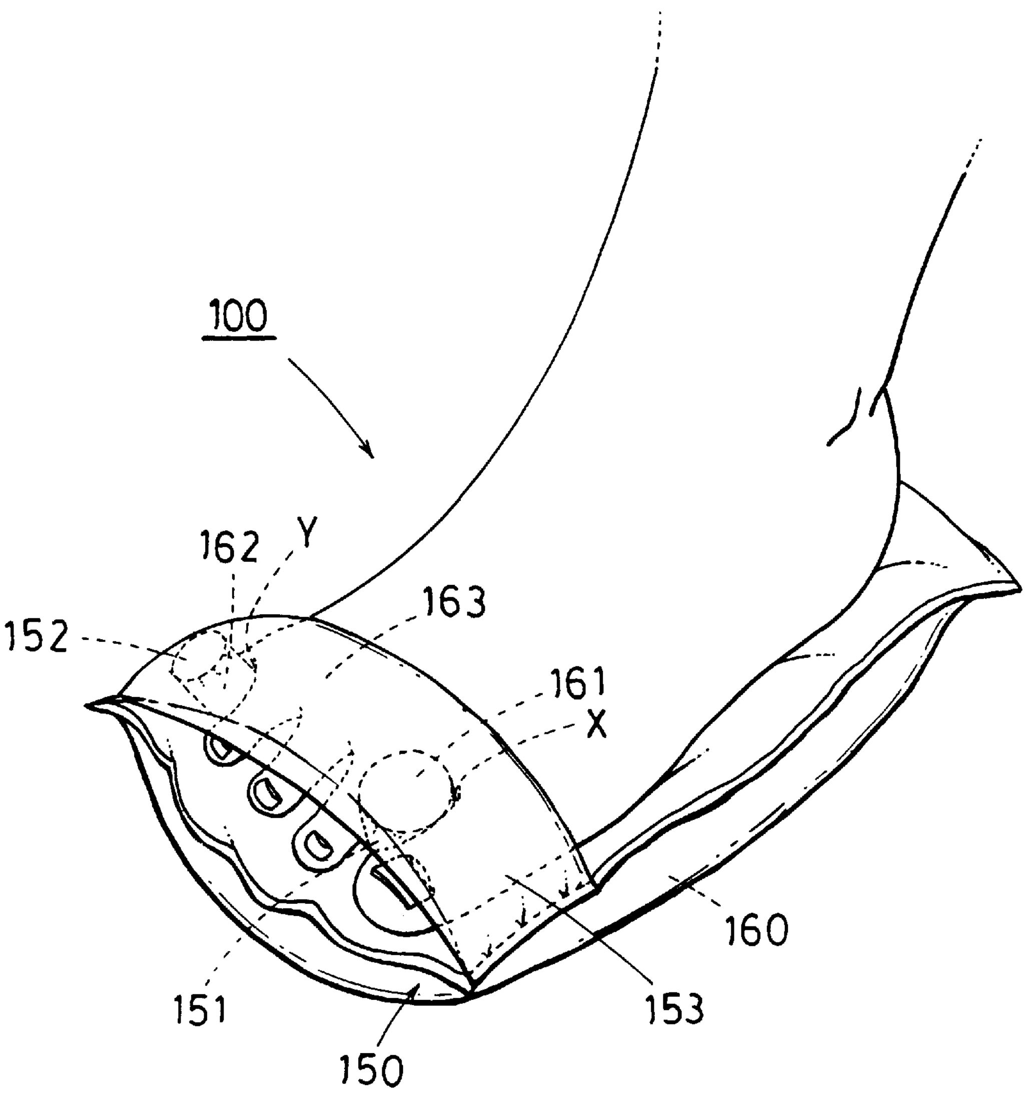
FIG. 10 is a perspective view showing a developed configuration of the health appliance shown in FIG. 9.

The illustrated health appliance 100 is structured so that the back contacting member 150 having the second pressurized medium charging portion is pressed from the outside to move the pressurized medium charged in the second pressurized medium charging portion to the first pressurized medium charging portions to expand them. However, the appliance may be modified such that a front contacting member which can contact the instep and which has in an interior thereof a third pressurized medium charging portion 163 may be provided instead of or in addition to the back contacting member 150, as shown in FIG. 10. In this modified embodiment, the fitting members may be expanded by applying pressure to the back contacting member or the front contacting member by hand.

Further, instead of the illustrated embodied forms of the health appliances 1, 10, 100 including the fitting members, the front contacting member and/or the back contacting member, other modifications can be made in the invention. For example, the health appliance can be formed into a sock form covering the entire foot (including an ankle) and having throughout the entire interior thereof a pressure medium charging portion. This modification can provide the effect of enabling the entire surface of the foot, not limited to the instep and the sole of the foot, to be pressed from around it, in addition to the effect of stretching or closing the toes at the webs. Thus, a more complicated and stronger massaging effect can be achieved.

Further, the health appliances 1, 10, 100, which in illustration are designed for the toes, may be- designed for the fingers. In the case of the health appliance for the fingers, the fitting members will have to have a larger coefficient of expansion, as compared with the health appliance for the toes.

Also, the health appliance 1, which in illustration is provided with the instantaneous exhaust valve 51 to alternate the expansion with the contraction to thereby produce the massaging effect, may be designed to have the expanding capability only, as in the health appliance 10.

Further, the health appliance having two or more fitting members may include a means for expanding not only the fitting members but also the front contacting member and/or the back contacting member to which those fitting members are fixed. Therefore, the toes or fingers can be stretched at their webs. Additionally, the health appliances 1, 10, 100 may be allowed to have a vibrating capability and equivalent to provide a massaging capability.

The health appliance 10, which in illustration is so configured that the fitting members 141–144 fitted at the webs can expand more at their upper portions projecting upwards from the toes than at the remaining portion, may also be configured so that the fitting members can expand uniformly.

Figure 5:
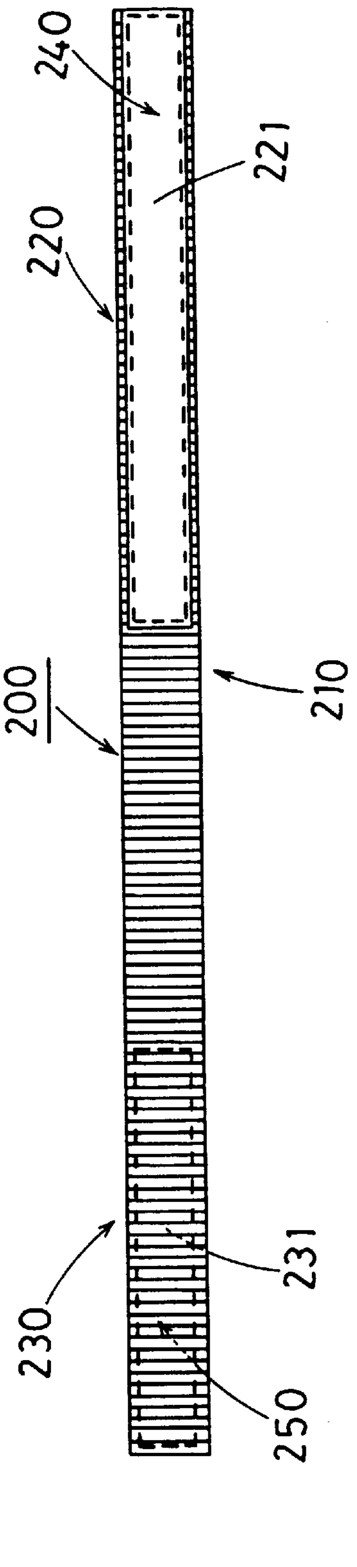
FIG. 5 is an illustration of a band as viewed from the top.
Figure 6:
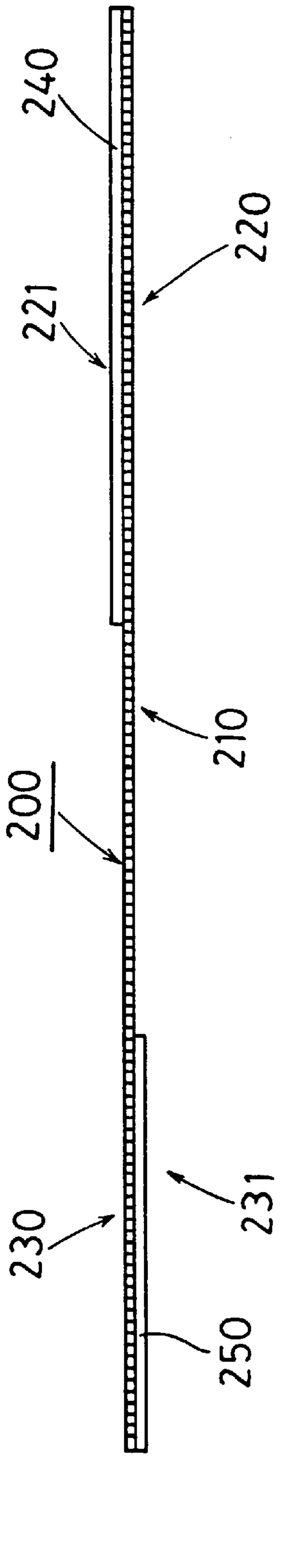
FIG. 6 is an illustration of the band as viewed from the side.

Further, it is effective (and particularly effective for hallux valgus) to use the health appliance 1 or 10 in combination with a band 200 having a detachably fastening portion at least at opposite ends thereof, as shown in FIGS. 5 and 6.

Now, the description on the band 200 will be given below. The band 200 is formed of a flexible tape 210 of 25 mm in width and 350 mm in length. On a front surface 221 at one end portion 220 of the band 200 is an engaging strip 240 having a number of loops (not shown) of 20 mm in width and 150 mm in length which is axed by stitching. On a back surface 231 at the other end portion 230 of the band 200 is an engaging strip 250 having a number of hooks (not shown) of 20 mm in width and 100 mm in length which is affixed by stitching.

In use, the band 200 is bound around the instep 8 (See FIG. 7), whereby the engaging strip 240 on the front surface 221 and the engaging strip 250 on the back surface 231 confront each other and are fastened together by engagement of a number of loops of the engaging strip 240 with a number of hooks of the engaging strip 250. Thus, the foot is tightened up by the band 200. The tightening strength of the belt can be adjusted by arbitrarily determining the amount of overlap of both engaging strips 240, 250 when the band is bound around the instep 8.

It will be understood that the dimensions of the widths and lengths of the tape 210 and the engaging strips 240, 250 mentioned above are illustrative only and may be made larger or smaller than the illustrated ones. Further, no particular limitation is imposed on the material of the tape 210, as long as it has flexibility. The materials which maybe used for the tape 210 include synthetic resins, non-woven fabrics, textiles, leathers, and extensible rubber belts or rings. Also, no particular limitation is imposed on the materials of the engaging strips 240, 250, as long as they have flexibility, and the materials which may be used for the engaging strips 240, 250 include synthetic resin tapes, non-woven fabrics and textiles.

In addition, the shapes of the tape 210 and the engaging strips 240, 250 are not limited to a rectangle as shown in FIGS. 5 and 6, and may also be formed in a polygon or an ellipse. No particular limitation is imposed on the shapes of the tape and the engaging strips, as long as they are elongated ones. Further, the engaging strips 240, 250 maybe affixed to the tapes 210 by adhesive bonding as well as by stitching.

Also, the affixing means may take any form for affixing the engaging strips 240 and 250 to each other, without being limited to the hooks and loops as illustrated above, as long as they have capabilities to bind each other. Instead of the engaging strips 240 and 250, hooks or buttons may be affixed to the end portions 220, 230 of the band 200 so that both end portions 220, 230 may be bound together by them.

Figure 7:
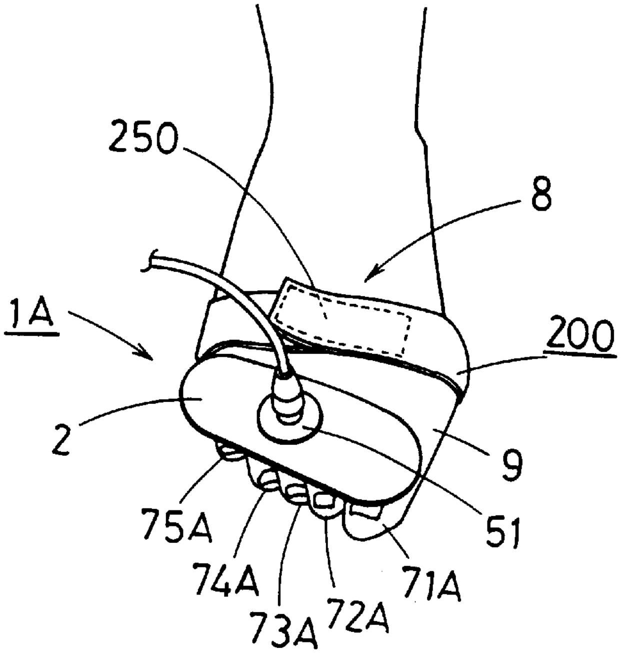
FIG. 7 is a perspective view of the band of FIG. 5 used in combination with the health appliance of FIG. 2 fitted to the toes.

Now, the use and operation of the health appliance 1 or 10 in combination with the band 200 will de described, with reference to FIGS. 3 and 7. The health appliance 1A shown in FIG. 7 is not different from the health appliance 1 shown in FIG. 3 in structure and operation, except in the shape of the front contacting member 2 at the four corners. Also, the band 200 used in combination with the health appliance 10 provides the same 10 operation and effect as the band used in combination with the health appliance 1. Accordingly, the description will be given below of the combined use of the band with the health appliance 1.

First, the health appliance 1 is fitted to the tip portion of the foot so that the fitting members 41, 42, 43 and 44 can be fitted in between the toes, respectively, as shown in FIG. 3. Before the air of the pressurized medium is charged into the pressurized medium charging portion, the band 200 is bound around the instep 8, passing around a ball of the foot or a projection 9 at the joint of the first finger 71A which is typical of the foot of hallux valgus, as shown in FIG. 7.

Then, air is charged into the pressurized medium charging portion until the pressurized medium charging portion is put into the expanded state to widen the spaces between the toes 71A, 72A, 73A, 74A and 75A. The pressurized medium charging portion is kept in the expanded state for a while, and thereafter the air filled in the pressurized medium charging portion is discharged out instantaneously by means of the instantaneous exhaust valve 51.

Figure 8:
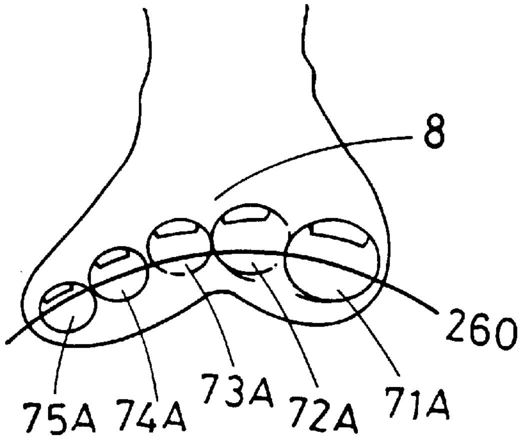
FIG. 8 is an illustration showing the toes aligned along an arcuate line.

This action is repeated by alternating the expansion with the contraction of the pressurized medium charging portion by charging and discharging the air therein and therefrom. Thus, the health appliance 1 used in combination with the band 200 bound around the instep 8 can provide the result that when the pressurized medium charging portion is filled with air, the toes can stretch at greater angles at their joints. This enables the toes of the foot of hallux valgus to be aligned along an arcuate line 260 (a curved line shown in FIG. 8), as a sound foot.

The band 200 may also be used for a foot of no hallux valgus as well as for a foot of hallux valgus. Also, in the case where the health appliance 1, 10 is used for a hand, the band 200 may be bound around the back of the hand for use in combination with the health appliance 1, 10.

What is claimed is:

1. A health apparatus comprising:

at least one fitting member for insertion in a space between toes, said at least one fitting member having an interior including an expandable charging chamber for receiving a pressurized medium so as to be charged with said pressurized medium;

a charging port communicating with said at least one fitting member, wherein said pressurized medium flows through said charging port into said charging chamber and charges said charging chamber so as to expand said at least one fitting member such that the space between the toes is increased; and a base member including a back member for contacting a sole of a foot and including a front member for contacting an area of the foot on top of the toes, said at least one fitting member being connected to said base member, wherein said base member has an interior including an expandable charging chamber for receiving said pressurized medium so as to be charged with said pressurized medium.

2. The apparatus of claim 1, wherein said at least one fitting member comprises a plurality of fitting members connected to said base member.

3. The apparatus of claim 1, further comprising a base member charging port communicating with said base member, wherein said pressurized medium flows through said base member charging port into said charging chamber of said base member so as to expand said base member such that said base member presses against the foot.

4. The apparatus of claim 3, wherein said at least one fitting member comprises a plurality of fitting members connected to said base member.

5. The apparatus of claim 1, wherein said charging chamber of said base member and said charging chamber of said fitting member are integrally formed so as to allow communication therebetween, said charging port communicating with said charging chamber of said base member and said charging chamber of said fitting member, wherein said pressurized medium flows through said charging port into said charging chamber of said base member and into said charging chamber of said fitting member so as to expand said fitting member such that the space between the toes is increased and so as to expand said base member such that said base member presses against the foot.

6. The apparatus of claim 5, wherein said at least one fitting member comprises a plurality of fitting members connected to said base member.

7. The apparatus of claim 1, wherein said charging port includes an exhaust valve, said exhaust valve having a preset relief pressure.

8. The apparatus of claim 1, further comprising an air compressor communicating with said charging port via an air hose.

9. A health apparatus comprising:

at least one fitting member for insertion in a space between toes, said at least one fitting member having an interior including an expandable first charging chamber for receiving a pressurized medium so as to be charged with said pressurized medium;

a back member for contacting a sole of a foot, said back member having an expandable second charging chamber communicating with said first charging chamber, wherein a pressurized medium in said second charging chamber is capable of flowing to said first charging chamber by pressing an exterior of said back member, whereby said at least one fitting member is expanded so as to increase the space between the toes; and a front member for contacting an area of the foot on top of the toes, said front member having an expandable third charging chamber communicating with said first charging chamber, wherein said pressurized medium in said third charging chamber is capable of flowing to said first charging chamber by pressing an exterior of said front member, whereby said at least one fitting member is expanded so as to increase the space between the toes.

10. The apparatus of claim 9, wherein said at least one fitting member comprises a plurality of fitting members connected to said base member.

* * * * *